US005641764A

United States Patent [19]
Martin et al.

[11] Patent Number: 5,641,764
[45] Date of Patent: Jun. 24, 1997

[54] HALOGENATED DNA LIGAND RADIOSENSITIZERS FOR CANCER THERAPY

[75] Inventors: Roger Francis Martin, Heidelberg; David Patterson Kelly, Canterbury, both of Australia

[73] Assignees: Peter MacCallum Institute; University of Melbourne; Anti-Cancer Council of Victoria, all of Victoria, Australia

[21] Appl. No.: 441,116

[22] Filed: May 15, 1995

Related U.S. Application Data

[63] Continuation of Ser. No. 768,588, filed as PCT/AU90/00122, Mar. 30, 1990, abandoned.

[30] Foreign Application Priority Data

Mar. 31, 1989 [AU] Australia ................................. PJ3468

[51] Int. Cl.$^6$ ........................ A01N 57/00; A61K 31/675
[52] U.S. Cl. ........................ 514/80; 514/79; 514/81; 544/364; 536/18.7
[58] Field of Search ..................... 514/44, 79, 80, 514/81; 544/364; 536/18.7, 27.1, 23.1; 548/306.1; 546/102, 104; 424/1.11

[56] References Cited

U.S. PATENT DOCUMENTS

| | | |
|---|---|---|
| 4,415,588 | 11/1983 | Cavazza . |
| 4,415,589 | 11/1983 | Cavazza . |
| 4,464,393 | 8/1984 | Cavazza . |
| 4,663,352 | 5/1987 | Onofrj . |
| 4,751,242 | 6/1988 | Calvani et al. . |
| 5,096,694 | 3/1992 | Quivy et al. ............... 424/1.11 |

OTHER PUBLICATIONS

Murray et al, Sequence Specificity of $^{125}$I-labelled Hoechst 33258 Damage in Six Closely Related DNA Sequences, *J. Mol. Biol.*, 203:63–73 (1988).
Murray et al, Sequence Specificity of $^{125}$I-labelled Hoechst 33258 in Intact Human Cells, *J. Mol. Biol.*, 201:437–442 (1988).
Russell et al, In Vitro and in Vivo Radiation Sensitization by the Halogenated Pyrimidine 5–Chloro–2'–deoxycytidine, *Cancer Res.*, 46:2883–2887 (1986).
Marcus, Clinical Photodynamic Therapy: The Continuing Evolution, pp. 219–268.
Teng et al, The Molecular Structure of the Complex of Hoechst 33258 and the DNA Dodecamer d(CGCGAATTCGCG), *Nucleic Acids Res.*, 16(6):2671–2690 (1988).
Martin et al, DNA Damage by Auger Emitters, Taylor & Francis, pp. 55–68 (1988).
Martin et al, Rapid Communication, Radiation Sensitization by an Iodine–labelled DNA Ligand, *Int. J. Radiat. Biol.*, 57(5):939–946 (1990).
Martin et al, DNA: A Molecular Framework for Studying Reactive Species, *Recueil des Travaux Chimiques des Pays–Bas*, 106:178 (1987).
Martin et al, Preparation of Carrier Free[$^{125}$I]IodoHoechst 33258, *Int. J. Appl. Radiat. Isot.*, 36(9):745–747 (1985).

Martin et al, Use of an $^{125}$I–labelled DNA Ligand to Probe DNA Structure, *Nature*, 302(5907):452–454 (1983).
Martin et al, Synthesis and N.M.R. Spectra of Substituted Aminoiodoacridines, *Aust. J. Chem.*, 32:2637–2646 (1979).
Martin et al, Cytotoxicity of an $^{125}$I–labelled DNA–binding Compound that Induces Double–Stranded DNA Breaks, *Cancer Res.*, 39:3244–3247 (1979).
Martin, Induction of Double–Stranded Breaks in DNA by Binding with an $^{125}$I–labelled Acridine, *Int. J. Radiat. Biol.*, 32(5):491–497 (1977).
Martin et al, Synthesis and Characterization of 2–Iodo–4–[5"–(4'''–methylpiperazin–1'''–yl)–2", 5'–bi–1H–benzimidazol–2'–yl]phenol (iodoHoechst 33258) and 2,5–Disubstituted Benzimidazole Model Compounds, *Aust. J. Chem.*, 39:373–381 (1986).
Rodriguez et al, Continuous Infusion of Halogenated Pyrimidines, *I. J. Radiation Oncology, Biology, Phsics*, 20(6):1380–1381 (1991).
Ridley et al, A New Synthesis of Benzimidazoles and Aza–analogs, *J. Het. Chem.*, 2:453–456 (1965).
Martin et al, Comparative Studies of UV–induced DNA Cleavage by Structural Isomers of an Iodinated DNA Ligand, *Int. J. Radiat. Oncol. Biol. Phys.* (in press) (1993).
Loewe et al, Basic–Substituted 2,6–Bisbenzimidazole Derivatives, a Novel Series of Substances with Chemotherapeutic Activity, *J. Arzneim.–Forsch.* (*Drug Res.*), 24:1927–1933 (1974) (with transl.).
Murray et al, The Degree of Ultraviolet Light Damage to DNA Containing Iododeoxyuridine or Bromodeoxyuridine is Dependent on the DNA Sequence, *Nucleic Acids Res.*, 17(7):2675–2691 (1989).
Adams et al, Structure–Activity Relationships in the Development of Hypoxic Cell Radiosensitizers, *Int. J. Radiat. Biol.*, 35(2):133–150 (1979).
Brown, Clinical Trails of Radiosensitizers: What Should We Expect?, *Int. Radiat. Oncol. Biol. Phys.*, 10:425–429 (1984).
Martin et al. Chem. Abstr. No. 106:32923b, p. 539, 1987; Aus. J. Chem. 39(2):373–381, 1986.
Sano et al. Chem. Abstr. No. 70:6805, p. 672, 1969; No to Shinkei, 19:339–344, 1967.
Smith et al. Chem. Abstr. 102:92205w, p. 269, 1985; Int. J. Radiation Biol. Relat. Stud. Phys. Chem. Med. 46(4): 331–334, 1984.
Martin et al. Chemical Abstracts 93:46379d, 1980, Aust. J. Chem. 32(12):2637–2646, 1979.
Murray et al. J. Mol. Biol. 201:437–442, 1988.

*Primary Examiner*—John Kight
*Assistant Examiner*—Dameron L. Jones
*Attorney, Agent, or Firm*—Sughrue, Mion, Zinn, Macpeak & Seas

[57] ABSTRACT

A radiosensitizer for use in radiotherapy comprises a halogenated DNA ligand. The susceptibility of DNA to radiation damage is enhanced by causing or allowing the halogenated DNA ligand to bind to the DNA before subjecting the DNA or the locus thereof to ionizing or ultraviolet radiation. Radiation damage in DNA is also induced by causing or allowing a halogenated DNA ligand to bind to DNA and irradiating the DNA and said bound ligand or the locus thereof with ionizing or ultraviolet radiation.

10 Claims, 5 Drawing Sheets

```
                                          →
                                 →  →  →  → 30
                        →        →
                 →  →     →
         →
                4350      4360       10          20          30
                          gaggcccTTTcgtcttcaagAA TTctcatgTTTgacagcTTTATcatcgATAAgct
                          ctccgggAAAgcagaagttCTT AAgagtacAAAActgtcgAATAgtagcTATTcga
                4350      4360       10          20          30
                          ←
                                 ←       ←      ←
                                      ←•  ←
                                 ←•          •← 
                4350      4360       10          20          30
```

5'-³²P-E375B pip⁺/pip⁻
D100H-3'-³²P pip⁻
D100H-3'-³²P pip⁺

D100H-5'-³²P pip⁺/pip⁻
3'-³²P-E375B pip⁺
3'-³²P-E375B pip⁻

FIG. 3

UV/IODOHOECHST CLEAVAGE SITES IN CLONED HUMAN α DNA

| | | | | | |
|---|---|---|---|---|---|
| 32/33 | tgTTTca | S | 191 | ccTTTgt | S |
| 78 | tAAAca | S | 227 | ccTTTct | M |
| 88/89 | tcTTTTgt | S | 232 | tcTTTTca | VS |
| 97 | tgTAATTTgc | M | 245 | agTTAgg | M |
| 112 | agATTTca | S | 250 | ggAAAca | M |
| 122 | gcTTTga | VS | 260 | tgTTTgt | S |
| 131/132 | tcAATgg | S | 265 | gtAAAgt | M |
| 140 | agAAAAgg | S | 282 | ggATATTca | M |
| 157 | ccTATAga | M | 310 | ggAAAcg | S |
| 160/161 | agAAAct | M | 318 | ggATTTct | S |
| 172 | agAATga | S | 327 | gcATATTgc | S |
| 176 | tgATTgc | S | 344 | agAATTc | M |

FIG. 5

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
    ( A ) LENGTH: 55 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( x i ) SEQUENCE DESCRIPTION: SEQ ID NO:1:

GAGGCCCTTT CGTCTTCAAG AATTCTCATG TTTGACAGCT TATCATCGAT AAGCT                55

( 2 ) INFORMATION FOR SEQ ID NO:2:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( x i ) SEQUENCE DESCRIPTION: SEQ ID NO:2:

TTCGAATAGC TACTATTCGA CAGTTTGTA                                             29

( 2 ) INFORMATION FOR SEQ ID NO:3:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( x i ) SEQUENCE DESCRIPTION: SEQ ID NO:3:

TGTAATTTGC                                                                  10

( 2 ) INFORMATION FOR SEQ ID NO:4:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i i ) MOLECULE TYPE: DNA (genomic)

```
( i i i )  HYPOTHETICAL: NO ( i v )  ANTI-SENSE: NO ( v )  FRAGMENT TYPE: internal ( x i )  SEQUENCE DESCRIPTION: SEQ ID NO:4:

GCATATTATG C                                                                                              1 1
```

HALOGENATED DNA LIGAND RADIOSENSITIZERS FOR CANCER THERAPY

This is a continuation of application Ser. No. 07/768,588 filed Nov. 4, 1991, now abandoned.

This invention relates to the use in cancer therapy of halogenated DNA ligands which induce radiation damage in DNA in response to ionising or ultraviolet radiation. More particularly, the invention is concerned with the use of such ligands as radiosensitisers.

Radiosensitisers are substances which when present during irradiation, enhance the cytotoxic effects of radiation. For example, the hypoxic radiosensitiser Misonidazole, enhances the cytotoxic effect of X- and γ-radiation. Although studied for many years, the interaction between radiation and radiosensitiser is complex and difficult to predict. Moreover, as both the radiosensitiser and the radiation are cytotoxic per se, their use in therapy is limited.

Photosensitisers are substances which when present, enhance the cytotoxic effects of ultraviolet or visible radiation. For the purposes of this specification photosensitisers are included in the term radiosensitisers.

The term ionising radiation is used herein to include photons having enough energy to ionise a bond, such as, α, β, γ rays from radioactive nuclei and x-rays.

Incorporation of a bromine or iodine atom into DNA using BUdR or IUdR is known to sensitise DNA to breakage by ionising or ultraviolet radiation. The sensitisation is mediated by the uracilyl free radical formed by dissociation of the carbon-halogen bond in the BUdR or IUdR by UV and the same free radical is formed by a reaction of hydrated electrons produced by ionising radiation. It has been proposed that the uracilyl free radical initiates strand cleavage by abstraction of the hydrogen atom from the 2'-deoxyribose carbon on the adjacent nucleotide.

We have investigated the induction of DNA strand breaks by UV-irradiation of DNA-bound iodoHoechst 33258 (4-[5"-(4'"-methylpiperazin-1'"-yl)- 2", 5'-bi-1H-benzimidazol-2'-yl]phenol), a sequence-selective DNA ligand that binds in the minor groove of DNA. Analysis of the fragmentation products on DNA sequencing gels indicates that strand cleavage results from hydrogen atom abstraction at the 5'-deoxyribose-carbon, by analogy with cleavage by neocarcinostatin. It is believed that photolytic deiodination of the DNA ligand leaves a carbon-centred free radical adventitiously located in the minor groove, resulting in hydrogen atom abstraction and consequent strand cleavage.

We have also found that the iodinated DNA ligand is a potent sensitiser of cell-kill by near UV. When the ligand is attached to the DNA, irradiation with ionising or ultraviolet radiation generates free radicals very close to, but not actually on, the DNA. DNA breaks are produced following abstraction of hydrogen atoms from DNA near the binding sites of the halogenated ligand. Our results indicate that halogenated DNA ligands may also act as sensitisers of ionising radiation. Ultraviolet radiation is more effective at producing free radicals than ionising radiation. However, ultraviolet radiation has a low tissue penetration and could only be used in the treatment of superficial tumours or in the specific killing of isolated tumour cells for example, in samples of bone marrow prior to bone marrow transplantation.

Thus, according to one aspect of the present invention there is provided a radiosensitiser for use in cancer therapy which comprises a halogenated DNA ligand.

According to another aspect of the present invention there is provided a method for enhancing the susceptibility of DNA to radiation damage, which comprises causing or allowing a halogenated DNA ligand to bind to the DNA before subjecting the DNA or the locus thereof to ionising or ultraviolet radiation.

According to a further aspect of the present invention there is provided a method for inducing radiation damage in DNA, which comprises causing or allowing a halogenated DNA ligand to bind to DNA and irradiating the DNA and said bound ligand or the locus thereof with ionising or ultraviolet radiation.

The DNA ligand may be of any suitable known type e.g. an intercalating ligand such as an aminoacridine or a minor groove binding ligand such as bis-benzimidazole and those described in Baguley, V. C., (1982) J. Mol. Cell. Biochem. 43: 167–181, for example, compounds having the following structural formulae:

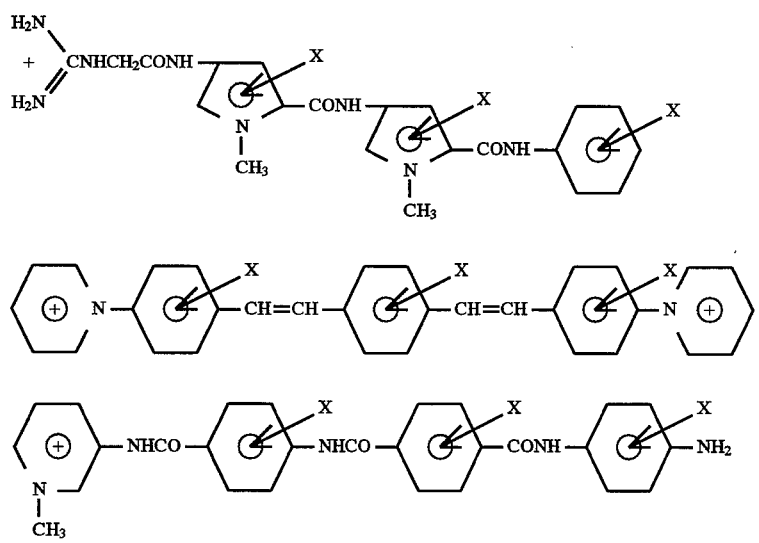

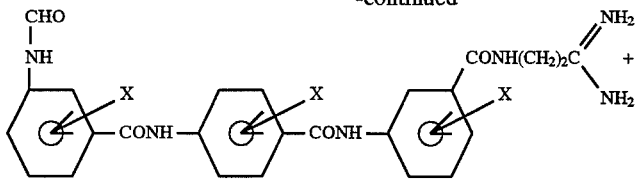

wherein X is halogen.

Advantageously, the ligand (with its attached halogen atom) is of a type which allows enhanced uptake, by endocytosis or other means, of the radiosensitiser into cells.

In a preferred embodiment the minor groove binding ligand is a halogenated bis-benzimidazole of the general formula:

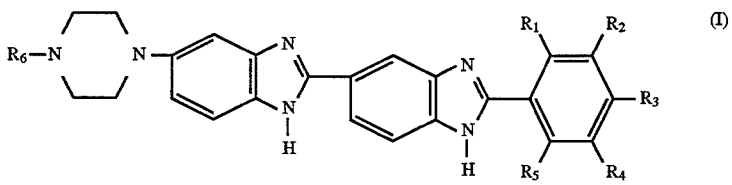

wherein $R_1$, $R_2$, $R_3$, $R_4$ and $R_5$, which may be the see or different, are selected from the group consisting of hydrogen, halogen, hydroxy, alkoxy, nitro or any other suitable non-deleterious substituent; and $R_6$ is alkyl; phenyl; phenyl optionally substituted with halogen, hydroxy, alkoxy, nitro or any other suitable non-deleterious substituent; or phenylalkyl optionally substituted with halogen, hydroxy, alkoxy, nitro or any other suitable non-deleterious substituent.

Particularly preferred compounds of formula (I) are those wherein $R_1$, $R_2$, $R_3$, $R_4$ and $R_5$, which are either the same or different, are selected from hydrogen, hydroxy, alkoxy, iodo and bromo; and $R_6$ is methyl, phenyl or phenylalkyl.

The halogenated ligand is preferably selected so as to bind at a location near the sugar chain of DNA so that the halogen free radical is sufficiently close to the potential target area in the sugar chain.

The basis of the invention is further shown by reference to the accompanying drawings in which:

FIG. 3 shows the pBR322 restriction fragment used in the experiments involving higher resolution (16% acrylamide) sequencing gels (SEQ ID NO. 1);

FIG. 5 shows the analysis of a large number of binding sites of DNA substrates derived from M13 clones of human alpha-DNA (SEQ ID NOS. 3 and 4).

Details of the experimental methods are given in the Examples which follow.

The UV spectrum of Hoechst 33258 has an absorption maximum at 338 nm which shifts to 356 nm upon binding to DNA. Substitution of iodine with the phenyl ring of the bis-benzimidazole shifts the maximum to 345 nm. Therefore, UV-A (320–400 nm) was used in preference to UV-B which closely coincides with the absorption of the halogenated nucleotides.

Figure 1:
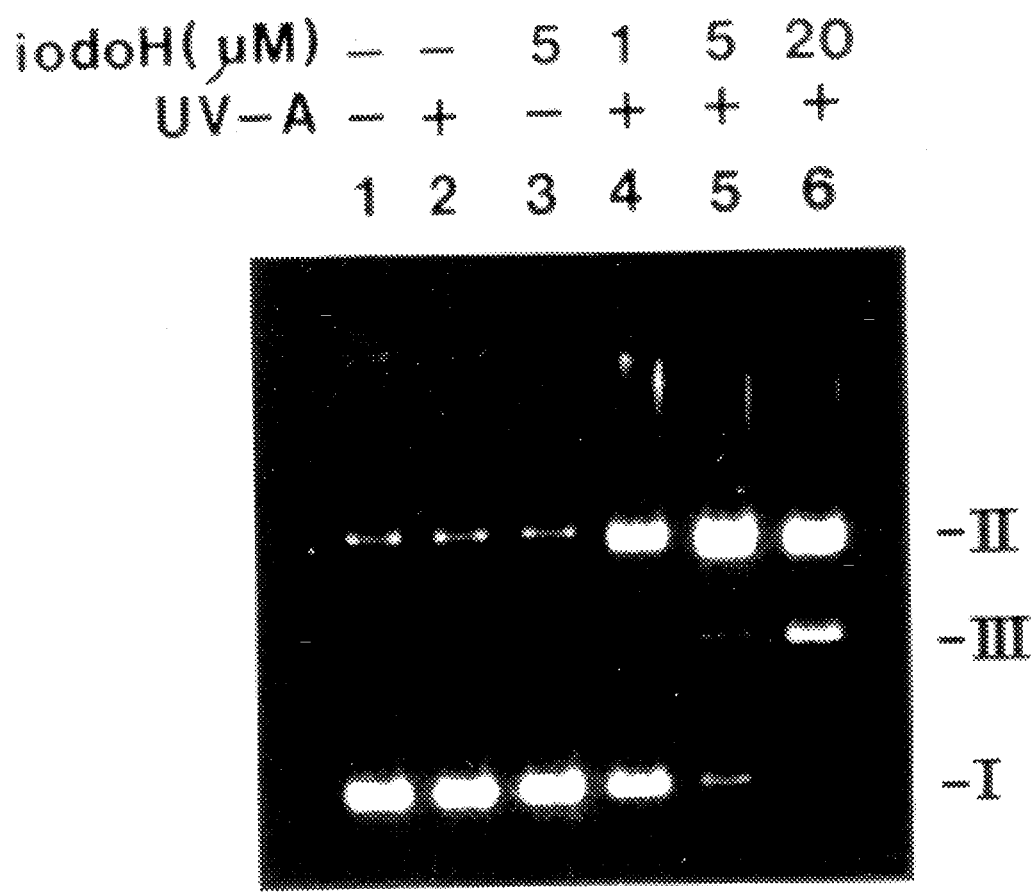
FIG. 1 shows the 1.7% agarose gel of UV-B irradiated mixtures of plasmid DNA and iodoHoechst 33528.

Irradiation of mixtures of plasmid DNA and iodoHoechst 33258 clearly resulted in marked strand cleavage (FIG. 1) which was detectable at input ratios below one DNA ligand per 50 bp. No detectable cleavage was obtained by UV irradiation of DNA with the same dose of UV-A in the presence of unsubstituted Hoechst 33258 (not shown), nor with UV irradiation only.

Similar results have been obtained with the following compounds of formula (I) wherein $R_1=R_4=R_5=H$, $R_2=I$, $R_3=OH$, $R_6=CH_3$;

$R_1=R_5=H$, $R_2=R_4=I$, $R_3=OH$, $R_6=CH_3$;

$R_1=R_4=R_5=H$, $R_2=I$, $R_3=OCH_3$, $R_6=CH_3$;

$R_1=R_5=H$, $R_2=R_4=I$, $R_3=OCH_3$, $R_6$—$CH_3$; and $R_1=R_3=R_4=R_5=H$, $R_2=Br$, $R_6=CH_3$.

Figure 2:
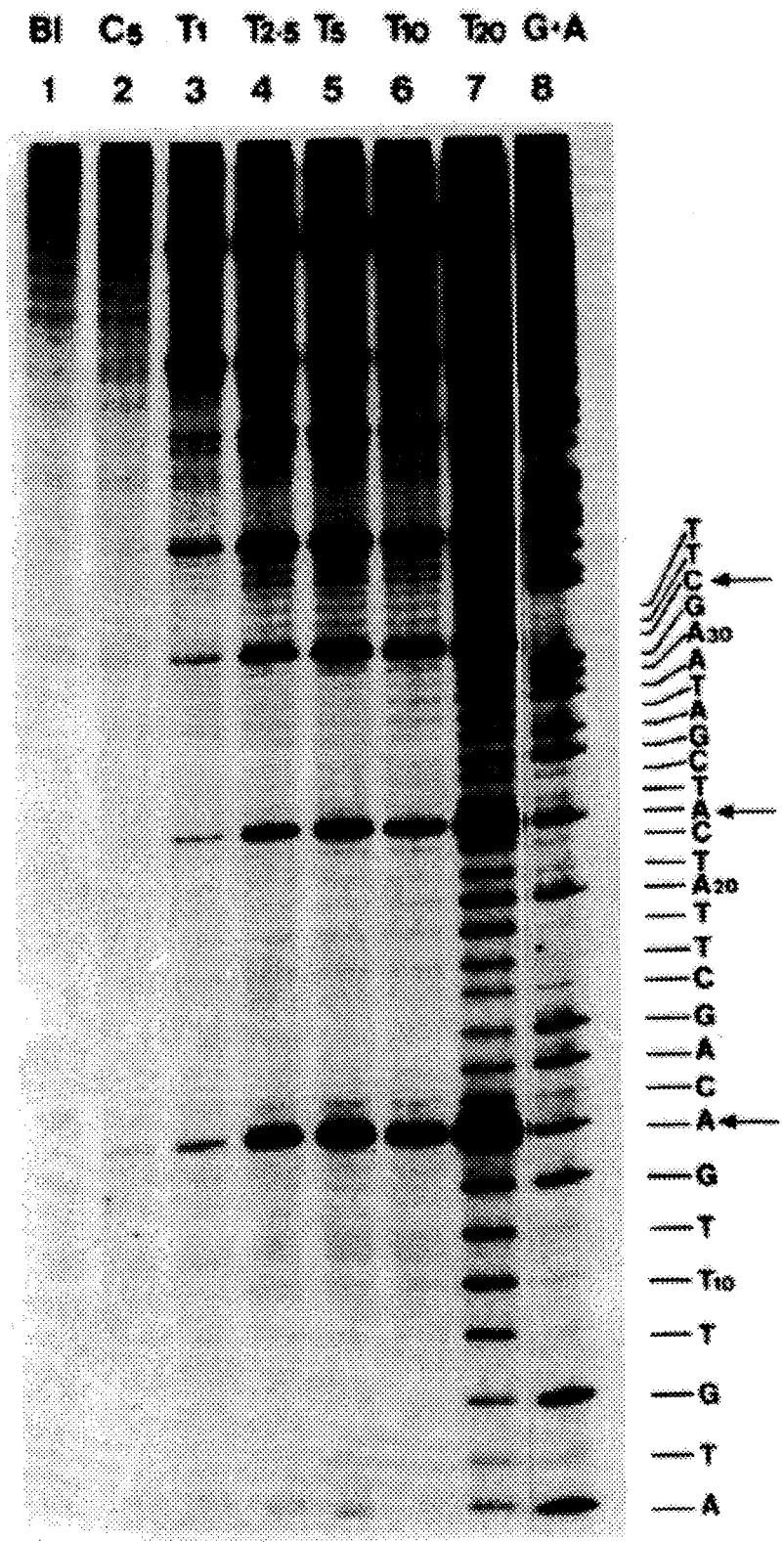
FIG. 2 shows the DNA-sequencing gels of fractionated 5'-$^{32}$P-end-labelled restriction fragment cleavage products (SEQ ID NO. 2)

To analyse the strand breaks in more detail 5'-$^{32}$P-end-labelled restriction fragments were used and the cleavage products were fractionated on DNA-sequencing gels. As illustrated in FIG. 2, these experiments showed that the UV-induced cleavage was at discrete sites along the DNA and always Just to the 3' side of a ligand binding site comprised of 3 or more consecutive AT base pairs. The extent of breakage generally increased with higher concentrations of the iodinated ligand but at 20 μM (compared to 75 μM DNA bp) more generalised breakage was apparent. Experiments with DNA substrate derived from M13 clones of human alpha-DNA enabled the analysis of a large number of binding sites and for all the stronger cleavage sites, the cleavage occurred at the 3'-end of the indicated binding site. The results are set out in FIG. 5.

A more detailed appreciation of the mechanism of photolytic cleavage came from experiments with higher resolution (16% acrylamide) sequencing gels, using a 100 bp pBR322 restriction fragment end-labelled 3' or 5', at either end of the fragment (FIG. 3). With 5'-labelled target DNA, the site of cleavage is always 3' to the ligand binding site and the mobility of the cleavage products coincide with corresponding bands in the Maxam-Gilbert sequencing tracks, regardless of whether or not the photolysis samples are treated with hot piperidine. On the other hand, the situation was more complex for experiments with 3'-labelled target DNA fragments. The major 3'-labelled fragment species was always about 2 nucleotides longer than anticipated from the 5'-labelled data, and its mobility sometimes different from the "nearest" Maxam-Gilbert band.

Alternatively, treatment of the photolysis samples with hot piperidine shortened the major species, bringing the cleavage site to the same nucleotide as seen for the corresponding 5'-labelled experiment. Moreover, the mobility of the piperidine-treated 3'-labelled species was coincident with the Maxam-Gilbert band. This pattern of mobilities is exactly the same as that described for neocarcinostatin cleavage of DNA.

Extensive investigations have indicated that a free radical species in neocarcinostatin abstracts a hydrogen atom from the 5'-carbon of deoxyribose and that subsequent oxidation at that carbon results in a strand break leaving the termini of a 5'-carbon aldehyde and 3'-phosphoryl. Subsequent piperidine treatment removes the base-sugar aldehyde leaving a 5'-phosphoryl group.

It is concluded by analogy that iodoHoeshst 33258 photolysis involves a similar cleavage mechanism, initiated by photolysis of the carbon-iodine bond and formation of a carbon-centred free radical on the DNA ligand, which subsequently abstracts a hydrogen atom from the 5'-carbon.

Figure 4:
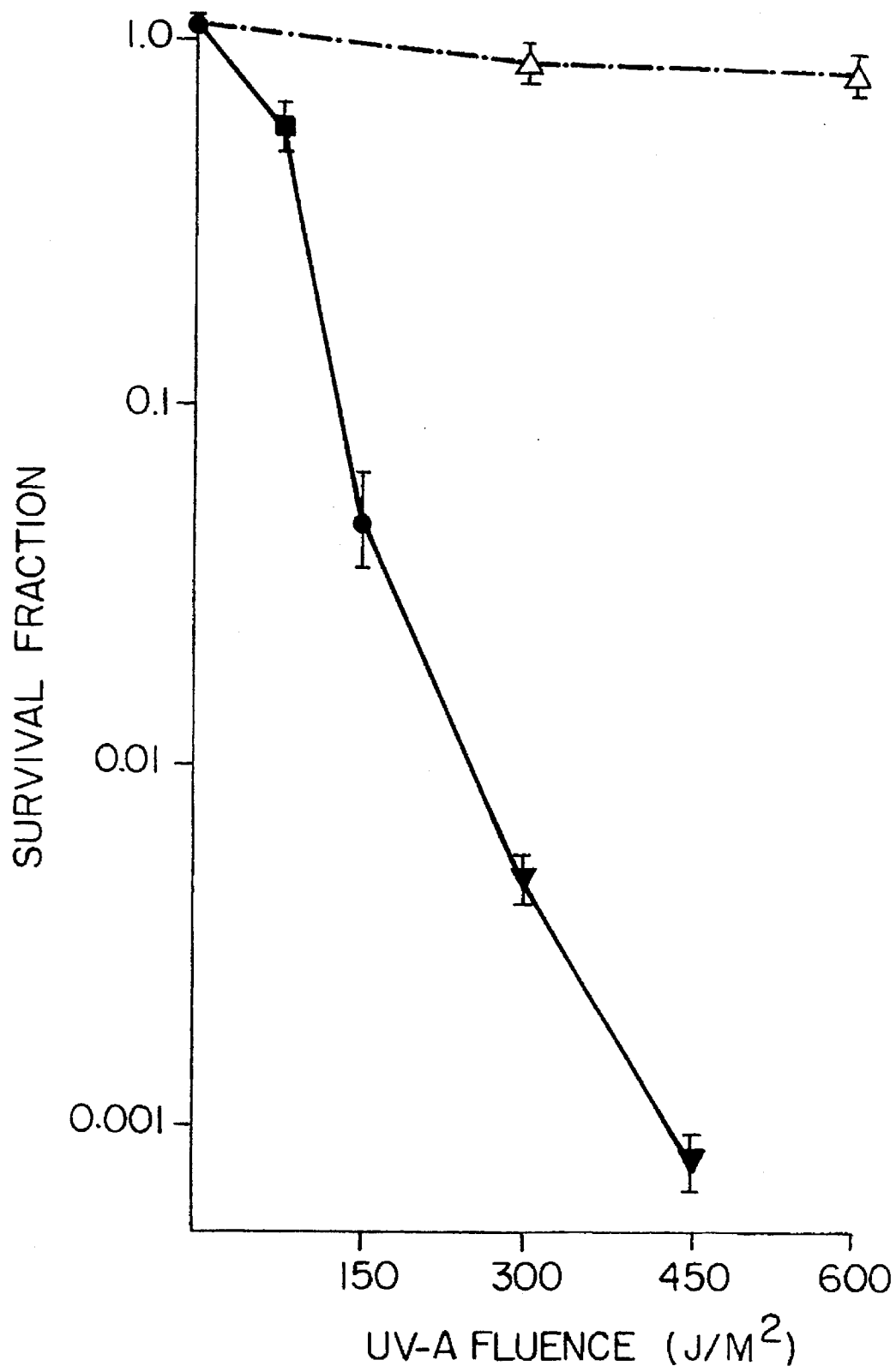
FIG. 4 shows the relationship between UV-A dose and cell survival when iodoHoescht is added to the cell medium to a concentration of 4 μM.

Cytotoxicity studies have shown that iodoHoechst is also a potent sensitiser in situ. When the DNA ligand was added to the medium to a concentration of 4 µM, irradiation resulted in 3–4-log cell kill at a UV-A dose that only marginally reduces cell survival in the absence of a sensitiser (FIG. 4). It is believed that the cell kill is mediated by DNA strand breakage.

Details of the above results and experimental procedures are given in the non-limiting Examples which follow.

The following abbreviations are used:
PBS phosphate buffered saline
EDTA ethylene diamine tetraacetic acid

EXAMPLE 1

(FIG. 1)

Mixtures containing pBR322 DNA (1 µg) and various amounts of HPLC-purified iodoHoechst 33258, in 20 µl of 5 mM Tris (PH 7.5)/20 mM NaCl/1 mM EDTA were irradiated for 20 minutes in an open 1.5 ml Eppendorf tube under a UV-A lamp, at a measured fluence of 75 µW cm$^{-2}$ (UV Radiometer with UVX-36 detector; U.V. Products, California, USA). The samples were fractionated on 1.7% agarose gels containing ethidium bromide. Control samples (lanes 1 and 3) were not irradiated and kept in the dark. A further control was irradiated but did not contain iodoHoechst (lane 2). The final iodoHoechst concentrations in the samples were 1 µM (lane 4), 5 µM (lanes 3 and 5) and 20M (lane 6).

EXAMPLE 2

(FIG. 2)

EcoR1-cut pBR322 DNA was 5'-$^{32}$P-end labelled, cut with BamH1 and the 375 bp labelled fragment isolated by preparative polyacrylamide gel electrophoresis. Samples of the labelled fragment were mixed with carrier DNA and iodoHoechst 33258 and photolysed as described in Example 1. The final concentrations of iodoHoechst were 1 µM (lane 1), 2.5 µM (lane 4), and 5 µM (lanes 2 & 5), 10 µM (lane 6), 20 µM (lane 7), and 40 µM (lane 8). The samples with matched amounts of $^{32}$P were then analysed on a 16% polyacrylamide sequencing gel. Samples for lanes 1 and 2 were unirradiated controls and lane 8 was a Maxam-Gilbert G+A track.

EXAMPLE 3

(FIG. 3)

End-labelled restriction fragments were derived from pBR322. The 375 bp fragments were prepared by 3'- or 5'-$^{32}$P end labelling at the EcoR1 site, followed by subsequent cleavage with BamH1 and then isolation by preparative polyacrylamide gel electrophoresis. Similarly, the 100bp fragments were obtained by end-labelling at the Hind IV site and subsequent cleavage with DdeI and preparative electrophoresis. Samples of each of the four labelled fragments were mixed with carrier DNA and subjected to UV-A photolysis with 5 µM iodoHoechst 33258 as described in Example 1. The samples were then analysed on 16% sequencing gels together with Maxam-Gilbert sequencing samples as in Example 1. In some cases (denoted pip$^+$) the photolysed samples were subjected to treatment with 1M piperidine at 90° C. for 30 minutes prior to sequencing gel analysis. The arrows indicate the sites of photolysis cleavage relative to Maxam-Gilbert references bands. The intensity of the bands vary considerably. The asterisked arrows denote particularly weak sites. The bp number in the pBR322 nucleotide sequence is shown and the sequence is aligned with the zero in each number.

EXAMPLE 4

(FIG. 4)

Mid-log phase V79 cells in 5ml alpha-MEM with 10% foetal calf serum in 25 cm$^2$ plastic flasks were incubated in the dark with 4 µM iodoHoechst 33258 (HPLC purified) for 2 hours at 37° C. and then chilled on ice for 30 minutes. The cultures were kept on ice during UV-A irradiation. The flasks were irradiated from above. After allowing for attentuation by the flask and medium, the dose-rate delivered to the monolayer was calculated to be approximately 50 µW cm$^{-2}$. After the appropriate irradiation time (0–20 minutes) the flasks were covered with black adhesive vinyl, washed twice with ice cold PBS/EDTA and suspended with 2 ml, 0.01% Pronase. A portion of the cell suspension was washed twice with BSS, samples counted in a Coulter Counter, and various aliquots plated-out in 50 nun plastic petri dishes. The colonies were fixed and stained after 7 days and the colonies of >50 cells scored. The control cloning efficiency (>60%) was used to calculate the relative cloning efficiency of treated cells. The data shown are derived from four separate experiments, indicated by different symbols. Open symbols depict controls without iodoHoechst 33258.

EXAMPLE 5

(FIG. 5)

Clone alpha 32, which contains a 340 bp insert of human alpha RI-DNA in M13 mp9, was effectively 5'-end labelled as described below and UV irradiated in the presence of iodoHoechst 33258 as described in Example 1. Autoradiographs of DNA sequencing gels were analysed by laser densitometry and damage sites were quantified as very strong (VS), strong (S) or medium (M). DNA sequences are presented 5' to 3' left to right In FIG. 5, the cleavage site is underlined and its position is given to the left of the DNA sequence. The iodoHoechst 33258 binding site is in capital letters.

The procedure for effectively 5'-end labelling M13 clone alpha 32 briefly involves pulse labelling the DNA immediately after the 17 bp sequencing primer with [$^{32}$P]dATP, dGTP and dCTP (which effectively labels the synthesised strand at the 5'-end). This is followed by a chase with cold dATP and dTTP, which results in extensive synthesis of DNA—greater than 3000 bp.

We claim:

1. A method for enhancing the susceptibility of DNA to radiation damage, which comprises causing or allowing a halogenated minor groove binding DNA ligand to bind to the DNA before subjecting the DNA, or the locus thereof, to ionizing or ultraviolet radiation.

2. The method as claimed in claim 1, wherein the halogenated minor groove binding DNA ligand is a halogenated bis-benzimidazole compound.

3. The method as claimed in claim 2, wherein the halogenated minor groove binding DNA ligand is a halogenated bis-benzimidazole represented by the following formula (I):

(a) causing or allowing a halogenated minor groove binding DNA ligand to bind to DNA; and (b) irradiating the DNA and said bound ligand, or the locus thereof, with ionizing or ultraviolet radiation.

7. The method as claimed in claim 6, wherein the halogenated minor groove binding DNA ligand is a halogenated bis-benzimidazole compound.

8. The method as claimed in claim 7, wherein the halogenated minor groove binding DNA ligand is a halogenated bis-benzimidazole represented by the following formula (I):

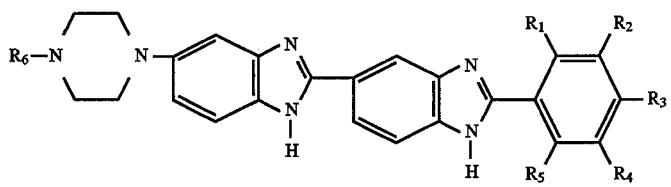

wherein $R_1$, $R_2$, $R_3$, $R_4$, $R_5$ and $R_6$, which are either the same or different, are selected from the group consisting of hydrogen; halogen; hydroxy; alkoxy; nitro; amino; alkyl; alkylphenyl; alkyl substituted with halogen, hydroxy, alkoxy, nitro or amino; alkylphenyl substituted with halogen, hydroxy, alkoxy, nitro or amino; alkenyl; alkenylphenyl; alkenyl substituted with halogen, hydroxy, alkoxy, nitro or amino; and alkenylphenyl substituted with halogen, hydroxy, alkoxy, nitro or amino, and wherein at least one of substituents $R_1$, $R_2$, $R_3$, $R_4$, $R_5$ or $R_6$ is halogen.

4. The method as claimed in claim 3, wherein $R_1$, $R_2$, $R_3$, $R_4$, and $R_5$, which are either the same or different, are selected from the group consisting of hydrogen, hydroxy, alkoxy, iodo and bromo; and $R_6$ is selected from the group consisting of methyl, phenyl and phenylalkyl.

5. The method as claimed in any of claims 1 to 4, wherein the halogenated minor groove binding DNA ligand is bound at a location near the sugar chain of DNA so that the halogen free radical is sufficiently close to the potential target area in the sugar chain.

6. A method for inducing radiation damage in DNA which comprises the steps of:

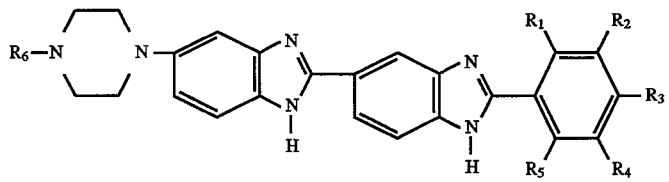

wherein $R_1$, $R_2$, $R_3$, $R_4$, $R_5$, and $R_6$, which are either the same or different, are selected from the group consisting of hydrogen; halogen; hydroxy; alkoxy; nitro; amino; alkyl; alkylphenyl; alkyl substituted with halogen, hydroxy, alkoxy, nitro or amino; alkylphenyl substituted with halogen, hydroxy, alkoxy, nitro or amino; alkenyl; alkenylphenyl; alkenyl substituted with halogen, hydroxy, alkoxy, nitro or amino; and alkenylphenyl substituted with halogen, hydroxy, alkoxy, nitro or amino, and wherein at least one of substituents $R_1$, $R_2$, $R_3$, $R_4$, $R_5$ or $R_6$ is halogen.

9. The method as claimed in claim 8, wherein $R_1$, $R_2$, $R_3$, $R_4$, and $R_5$ which are either the same or different, are selected from the group consisting of hydrogen, hydroxy, alkoxy, iodo and bromo; and $R_6$ is selected from the group consisting of methyl, phenyl and phenylalkyl.

10. The method as claimed in any one of claim 6 to 9, wherein the halogenated minor groove binding DNA ligand is bound at a location near the sugar chain of DNA so that the halogen free radical is sufficiently close to the potential target area in the sugar chain.

* * * * *